United States Patent
Saccomanno et al.

(10) Patent No.: US 7,151,604 B2
(45) Date of Patent: Dec. 19, 2006

(54) OPTICAL SYSTEM AND METHOD FOR PARTICLE DETECTION

(75) Inventors: Robert J. Saccomanno, Montville, NJ (US); Ivan B. Steiner, Ridgewood, NJ (US)

(73) Assignee: Honeywell International Inc., Morristown, NJ (US)

( * ) Notice: Subject to any disclaimer, the term of this patent is extended or adjusted under 35 U.S.C. 154(b) by 312 days.

(21) Appl. No.: 10/950,431

(22) Filed: Sep. 28, 2004

(65) Prior Publication Data

US 2005/0195605 A1   Sep. 8, 2005

Related U.S. Application Data

(63) Continuation-in-part of application No. 10/793,276, filed on Mar. 5, 2004.

(51) Int. Cl.
*G01N 21/00* (2006.01)

(52) U.S. Cl. .......................... 356/343; 356/337

(58) Field of Classification Search ............... 356/337, 356/338, 339, 340, 341, 342, 343; 250/222.2
See application file for complete search history.

(56) References Cited

U.S. PATENT DOCUMENTS

| | | | |
|---|---|---|---|
| 4,206,494 A | 6/1980 | Lovering | |
| 4,228,353 A * | 10/1980 | Johnson | 250/356.1 |
| 4,673,289 A | 6/1987 | Gaucher et al. | |
| 4,693,602 A * | 9/1987 | Wyatt et al. | 356/336 |
| 4,915,479 A | 4/1990 | Clarke | |
| 5,799,126 A | 8/1998 | Nagatani et al. | |
| 5,892,867 A | 4/1999 | Riser et al. | |
| 5,897,201 A | 4/1999 | Simon | |
| 6,086,234 A | 7/2000 | Riser et al. | |
| 6,238,074 B1 | 5/2001 | Hulse et al. | |
| 6,519,033 B1 * | 2/2003 | Quist et al. | 356/337 |
| 6,536,921 B1 | 3/2003 | Simon | |
| 6,553,168 B1 | 4/2003 | Saccomanno | |
| 6,573,992 B1 * | 6/2003 | Drake | 356/338 |
| 6,774,995 B1 * | 8/2004 | Quist et al. | 356/338 |
| 7,046,347 B1 * | 5/2006 | Amend et al. | 356/73 |
| 7,057,724 B1 * | 6/2006 | Mead et al. | 356/343 |
| 2002/0105806 A1 | 8/2002 | Foley | |
| 2002/0118362 A1 | 8/2002 | Saccomanno et al. | |
| 2003/0012533 A1 | 1/2003 | Steiner et al. | |
| 2003/0107734 A1 * | 6/2003 | Davis et al. | 356/338 |
| 2004/0159799 A1 | 8/2004 | Saccomanno et al. | |
| 2005/0195604 A1 | 9/2005 | Saccomanno et al. | |

FOREIGN PATENT DOCUMENTS

WO    WO 02/101289 A2    12/2002

\* cited by examiner

*Primary Examiner*—Gregory J. Toatley, Jr.
*Assistant Examiner*—Roy M. Punnoose
(74) *Attorney, Agent, or Firm*—Black Lowe & Graham PLLC

(57) ABSTRACT

In accordance with various embodiments, particle detection systems and method for particle detection are provided. In exemplary embodiments, the particle detection system includes at least one detector and a light source that provides light. The exemplary system can further include a radial collimator disposed surrounding a sample volume, wherein the radial collimator directs the light onto the sample volume. Various embodiments include an illumination morphing element having a light output end adjacent to the radial collimator and a light input end coupled to the light source. Various embodiments can also include a plurality of detection morphing elements wherein each of the plurality of detection morphing elements includes a light input end adjacent to the radial collimator and a light output end coupled to one or more of the at least one detectors.

33 Claims, 9 Drawing Sheets

OPTICAL SYSTEM AND METHOD FOR PARTICLE DETECTION

REFERENCE TO RELATED APPLICATIONS

This application is a continuation-in-part of application Ser. No. 10/793,276, filed Mar. 5, 2004, the disclosure of which is incorporated herein by reference.

TECHNICAL FIELD

The invention generally relates to systems and methods for detecting particles and, more particularly, to the field of cytometry.

BACKGROUND

Systems and methods for detecting, sorting, measuring, and imaging particles are useful in a variety of situations. The detection and analysis of the physical properties of biological particles, in particular, is generally referred to as cytometry. In conventional cytometry, a beam of light is projected through a fluid stream containing particles. When struck by the beam of light, the particles give off signals that are picked up by detectors. From these signals, information about the particles can be determined.

The signals generally fall into two categories. The first category is light scattered by the particles. The extent of scattering depends on physical properties of the particles, such as, the size, refractive index, and surface topography of the particles. Conventional cytometry uses multiple lenses placed in strategic locations to collect diffracted, reflected, and refracted light. One lens is typically located near the axis of the incident light to collect forward scattered light. Forward scattered light provides information about on the surface area or size of the particles. Another lens is typically placed at about ninety degrees to the incident light to collect side scattered light. Side scattered light provides information about the internal complexity of the particles. A series of beamsplitters and filters then steers the collected light to appropriate detectors.

The second general category of signals is fluorescence emitted by the particles. In order to measure biological and/or biochemical properties of interest, for example, cells are usually stained with fluorescent dyes that bind to specific portions of certain types of cells. When illuminated, the dyes absorb light energy over a particular range of wavelengths and emit fluorescence at wavelengths generally higher than that of the excitation light. Conventional cytometry collects the fluorescence with the same lens used to collect side scattered light. Fluorescence measurements can be used to identify particles and to provide limited quantitative information about the particles.

The amount of fluorescence emitted is proportional to the amount of dye molecules on the particles. Conventional cytometry lenses, however, detect only a small fraction of the emitted fluorescence. Problems also arise when the size range of the sample particles varies. In such cases, for example, the position of the detection lens may require re-positioning.

Thus, there is a need to overcome these and other problems of the prior art and to provide a particle detector and a method for its use.

SUMMARY OF THE INVENTION

According to various embodiments, the present teachings include a particle detector including at least one detector, a light source that provides light, and a radial collimator disposed surrounding a sample volume. The particle detector also includes an illumination morphing element comprising a light output end adjacent to the radial collimator and a light input end coupled to the light source. The particle detector further includes a plurality of detection morphing elements, each of the plurality of detection morphing elements comprising a light input end adjacent to the radial collimator and a light output end coupled to one or more of the at least one detectors.

According to various embodiments, the present teachings also include particle detector comprising, a detector, a light source that provides light, and a radial collimator disposed surrounding a sample volume. The particle detector also includes a plurality of illumination morphing elements, each of the plurality of illumination morphing elements comprising a light output end adjacent to the radial collimator and a light input end coupled to the light source. The particle detector further includes and a plurality of detection morphing elements, each of the plurality of detection morphing elements comprising a light input end adjacent to the radial collimator and a light output end coupled to the detector.

According to various embodiments, the present teachings include a method for particle detection including providing a barrel-shaped lens surrounding a sample volume. A light from a light source can be coupled to at least one illumination morphing element, wherein the illumination morphing element directs the light onto the barrel-shaped lens. The light can be directed onto the sample volume using the barrel-shaped lens. A sample light emitted by a plurality of particles that passes through the sample volume can be collected using the barrel shaped lens. The collected sample light can be coupled to a plurality of detection morphing elements disposed adjacent to the barrel-shaped lens. The sample light from the plurality of detection morphing elements can be directed to a first detector.

According to various embodiments, the present teachings further include a particle detector including at least one detector, a light source that provides light, and at least one optical element disposed to direct light from the light source to a sample area. The particle detector can also include a radial collimator disposed surrounding the sample volume. The particle detector can further include a plurality of detection morphing elements, each of the plurality of detection morphing elements comprising a light input end adjacent to the radial collimator and a light output end coupled to one or more of the at least one detectors.

It is to be understood that both the foregoing general description and the following detailed description are exemplary and explanatory only and are not restrictive of the present teachings, as claimed.

The accompanying drawings, which are incorporated in and constitute a part of this specification, illustrate several embodiments of the various embodiments and together with the description, serve to explain the principles of the present teachings.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

In the drawings.

DETAILED DESCRIPTION

In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, not to be taken in a limited sense.

FIGS. 1–8 disclose apparatus and methods for particle detection. Various embodiments include a radial collimator, a plurality of detection morphing elements to couple light collected by the radial collimator into optical fibers, and one or more illumination morphing elements to direct light from a light source to the radial collimator. As used herein, "radial collimator" means a lens or set of lenses disposed around a sample volume, capable of directing incident light to the sample volume, and collecting light emitted and scattered by particles in the sample volume. Also, as used herein, "morphing element" means a tapered optic that can be imaging or non-imaging, and in various embodiments can transition from a circular cross section to a polygonal cross section of larger area that can be tightly-packed.

Figure 1:
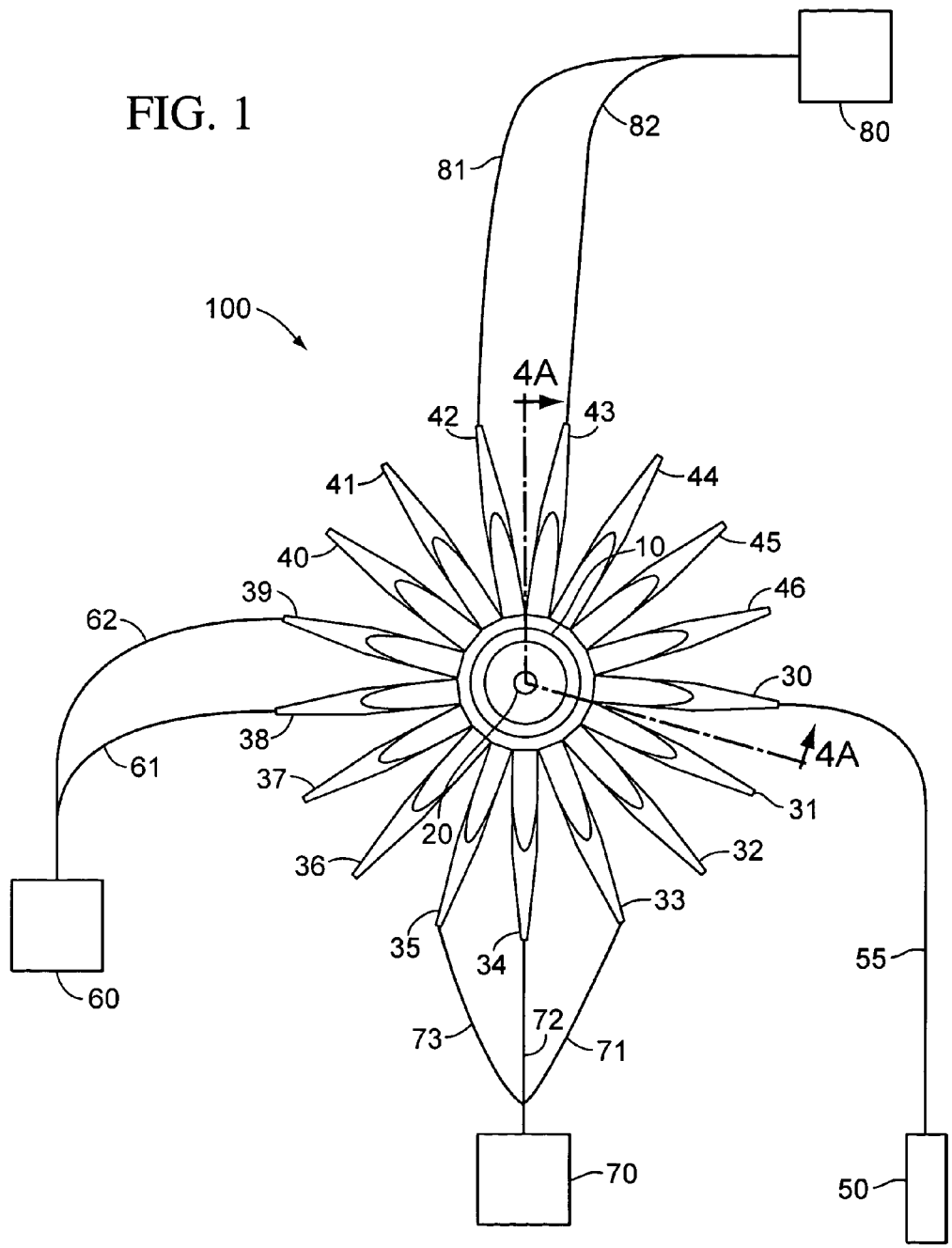
FIG. 1 depicts a top down view of a particle detection system in accordance with an exemplary embodiment of the invention.
Figure 2:
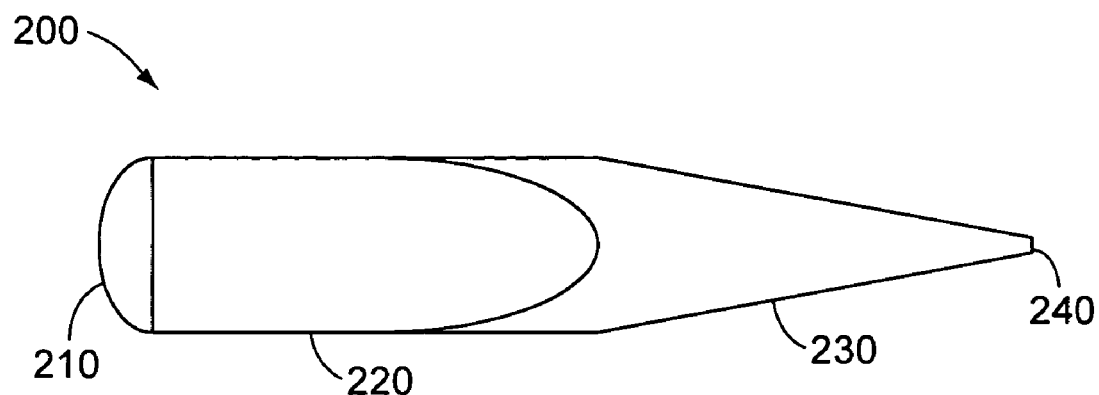
FIG. 2 depicts a morphing element including a plano-convex lens in accordance with an exemplary embodiment of the invention.

FIG. 1 depicts an exemplary particle detection system. FIG. 1 shows a top down view of a particle detection system 100 including a light source 50, a radial collimator 10, a plurality of morphing elements 30–46, and detectors 60, 70, and 80. Light source 50 can be any appropriate light source. For example, light source 50 can be one or more of a laser, an ultraviolet lamp, an LED, or any other high intensity, point-like source. A flow tube 20 can be used with a liquid or gas to transport particles to a sample volume (not shown).

Figure 7:
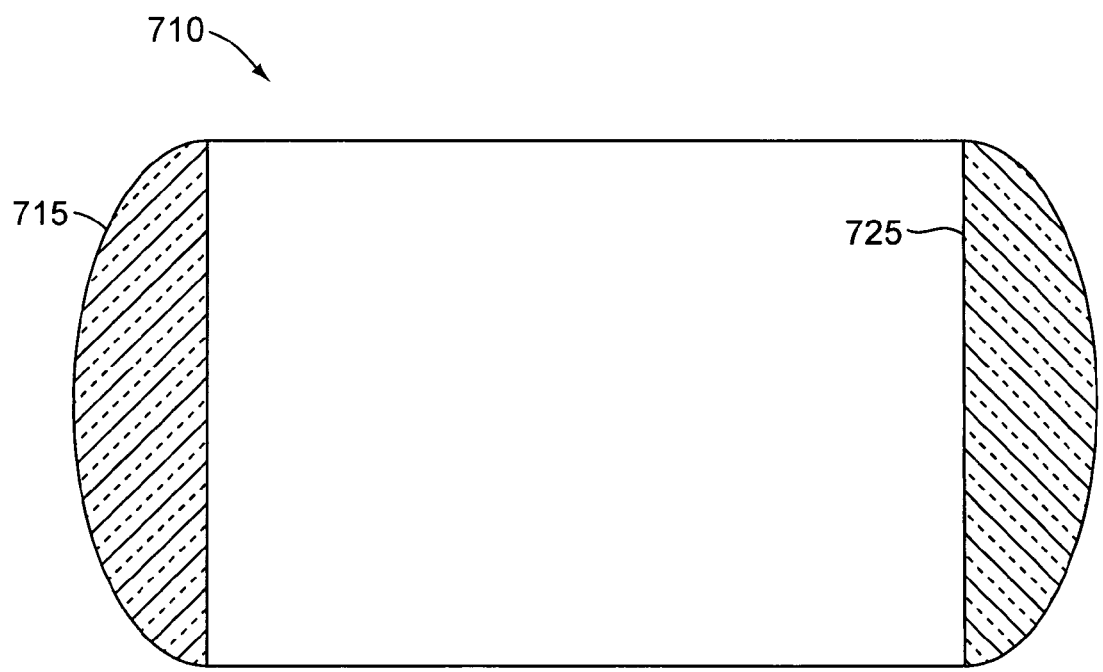
FIG. 7 depicts a sectional view of a radial collimator in accordance with an exemplary embodiment of the invention.

Radial collimator 10 can be positioned around flow tube 20. In various embodiments, flow tube 20 and radial collimator 10 can be aligned on a common centerline axis. FIG. 1 depicts radial collimator 10 comprising a single anamorphic lens surrounding flow tube 20. Referring to FIG. 7, various embodiments of the radial collimator can include a barrel-shaped lens. As used herein, the term "barrel-shaped lens" means a toroidal lens having a cylindrical or conical inner surface and a convex outer surface. Radial collimator 710 can comprise a cylindrical inner surface 725 and a convex outer surface 715. In an exemplary embodiment, the shape of convex outer surface 715 in cross sectional planes containing the toroid axis of rotational symmetry can be circular. Alternatively, outer surface 715 can have a non-circular shape. Radial collimator 710 can be made of, for example, borosilicate glass tubing turned on a lathe to form convex outer surface 715. Other appropriate lenses or systems of lenses can also be used by those familiar with the art of optical design not only for the anamorphic lens, but also for other lenses disclosed by this invention. Similarly, one familiar with the art of optical design can replace any of the optical elements disclosed by this invention, such as prisms or lenses, with more complex functionally equivalent or functionally superior optical elements, or systems of optical elements, known in the art.

Figure 3:
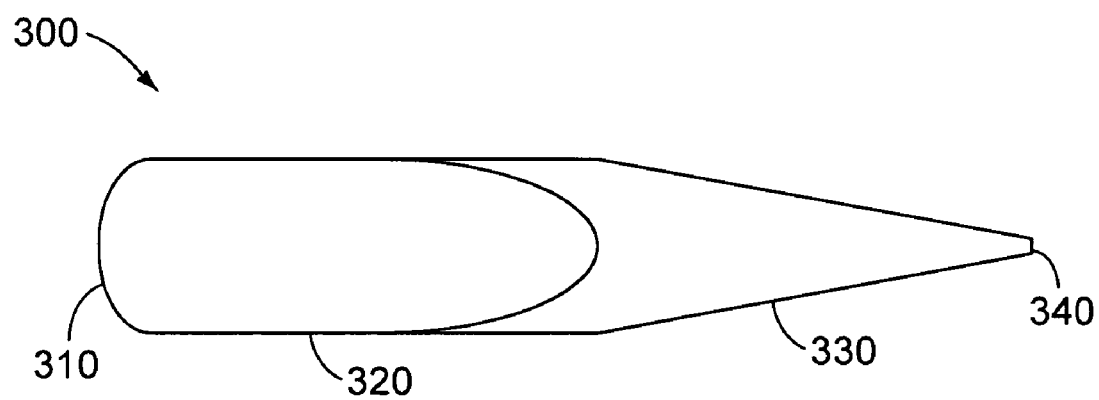
FIG. 3 depicts a morphing element having a convex end surface in accordance with an exemplary embodiment of the invention.
Figure 5A:
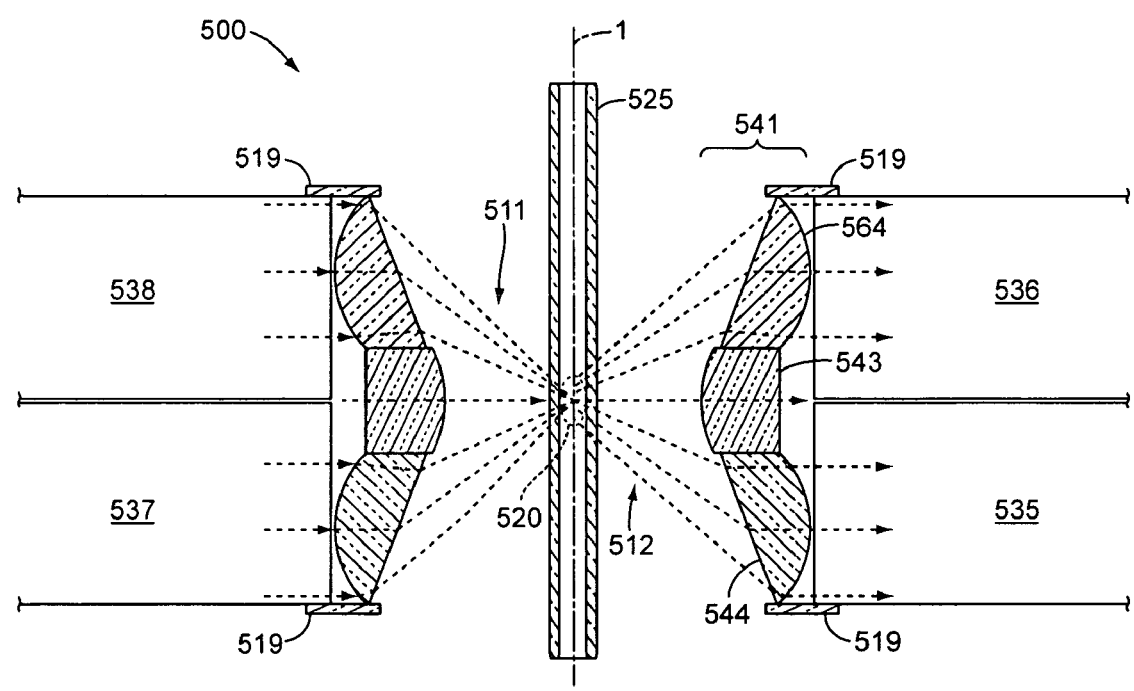
FIG. 5A depicts a sectional view of a particle detection system in accordance with an exemplary embodiment of the invention.

Morphing elements 30–46 can be positioned around radial collimator 10. One of skill in the art understands that the number of morphing elements shown in FIG. 1 is exemplary and that more or fewer morphing elements can be used. In various embodiments, each of morphing elements 30–46 can comprise two or more sections and can be imaging and/or non-imaging. For example, referring to FIG. 2, morphing element 200 can comprise at least two sections, a first section 220 and a second section 230. First section 220 can be polygonal in shape and positioned with a first end adjacent to the radial collimator. A plano-convex lens 210 can be positioned at the first end of first section 220. The plano-convex lens can be, for example, a cylindrical lens or cylindrical Fresnel lens. In another embodiment, as shown in FIG. 3, a convex surface 310 can be applied to the first end of first section 320 of morphing element 300. The convex surface can be, for example a cylindrical surface or cylindrical Fresnel surface. Each of morphing elements 30–46 can serve as an illumination morphing element or a detection morphing element. One of ordinary skill in the art will understand that the optical design of these ends and surfaces, in combination with that of radial collimator 10 shown in FIG. 1, can improve the collimation of light projected into first sections 220 and 320 of morphing elements 200 and 300, respectively, when used as detection morphing elements. Accordingly, it may be possible to increase the numerical aperture of radial collimator 10, for example as shown in FIG. 5A, in planes containing an axis 1 of radial collimator. In this manner, the light-capturing efficiency of radial collimator 10 can be increased. Lens 210 and end surface 310 collimate light intercepted from radial collimator 10 and project that light into first section 220 and/or 320, where it propagates by total internal reflection (TIR).

Partially collimated light from the radial collimator can be coupled into optical fibers when morphing elements 33–35, 38–39, and 42–43 shown in FIG. 1 are used as detection morphing elements. Accordingly, end 210 can be a light input end and end 240 can be a light output end. Similarly, end 310 can be a light input end and end 340 can be a light output end. As such, second section 230 captures light projected into it from section 220. Similarly, second section 330 can capture light projected into it from section 320. Second section 230 and/or 330 can comprise a conical shape to couple light into optical fibers (not shown) disposed at ends 240 and 340, respectively. In an embodiment, second sections 230 and/or 330 morph from a polygonal shape, such as, for example, a square or a rectangular cross section of section 220 and/or 320, to a round cross section and then taper, conically, to circular ends 240 and/or 340 adjacent to the optical fibers. The cross sectional area of ends 240 and/or 340 can be smaller than the cross sectional area of first section 220 and/or 320. In an embodiment, second sections 230 and/or 330 taper so that ends 240 and/or 340 adjacent to the optical fibers are circular in shape and have diameters approximately the same as that of the optical fiber. Morphing elements 30–46 can be made by methods known to those skilled in the art such as, for example, injection molding of a plastic material.

In various embodiments, each morphing element can be used as a detection morphing element or an illumination morphing element. When used as an illumination morphing element, light enters a light input end 240 from optical fiber 55. The light is then coupled into second section 230 from a light input end 240. Second section 230 then couples light into first section 220. The light exits the illumination morphing element at light output end 210. Similarly, second section 330 can couple light to first section 320 from an optical fiber disposed at light input end 340.

Detectors 60, 70, and 80 can convert the light signals into electrical signals. The electrical signals can then be amplified and digitized for further processing by instrumentation (not shown) known to one of ordinary skill in the art. Specific types of detectors can be selected by one of skill in the art and can include, for example, a photodiode or a photodiode array and a photomultiplier tube or a photomultiplier tube array.

Referring to FIG. 1, operation of an exemplary embodiment will be described. Light source 50 generates a light that can be coupled into optical fiber 55. Optical fiber 55 couples the light into a conical section, for example 230 in FIG. 2 and/or 330 in FIG. 3, of illumination morphing element 30. The conical section of illumination morphing element couples the light into the polygonal section, for example 220 in FIG. 2 and/or 320 in FIG. 3, of illumination morphing element 30. The light exits illumination morphing element 30 at a light output end, for example 210 in FIG. 2 and/or 310 in FIG. 3. Radial collimator 10 then focuses the light towards a sample volume within flow tube 20.

Particles in the sample volume of flow tube 20 can interact with the light, for example, by scattering the incident light and/or emitting fluorescence. Particles can be transported to the sample volume by methods known to one of ordinary skill in the art, such as, for example, transporting by a fluid in a capillary. Once within the sample volume, particles, either stationary and/or moving, can interact with the incident light. Radial collimator 10 collects the light, such as for example, the scattered light and/or fluorescence, and partially collimates the collected scattered light and/or fluorescence towards the input ends of the detection morphing elements. As used herein, "partially collimate" means having a smaller numerical aperture on the light output side of radial collimator 10 than the numerical aperture on the light input side of radial collimator 10. Accordingly, detection morphing elements 33–35, 38–39, and 42–43 collect the scattered light and/or fluorescence partially collimated by radial collimator 10 and couple that light into respective optical fibers 71–73, 61–62, and 81–82. One of skill in the art will understand that the number and configuration of the detection morphing elements shown in FIG. 1 is exemplary and that the number and configuration of the morphing elements can be arranged as desired. In an exemplary embodiment, detection morphing elements 38–39 can, for example, collect forward scattered light and detection morphing elements 42–43 can, for example, collect side scattered light. Detection morphing elements 33–35 can, for example, collect fluorescence.

Optical fibers 61–62, 71–73, and 81–82 can then transmit the collected scattered light and fluorescence to detectors 60, 70, and 80, respectively. The optical fibers can be physically coupled to morphing elements by, for example, an index matching fluid, or by other coupling alignment methods known to one of skill in the art. One of skill in the art will understand that the optical fiber configuration shown in FIG. 1 is exemplary and can include other optical components. For example, optical filters can be used between radial collimator 10 and detectors 60, 70, and/or 80 to select a desired wavelength for detection.

In various embodiments, light from light source 50 can be coupled into a plurality of morphing elements, for example, 30–32 and 44–46 of FIG. 1. Illumination morphing elements 30–32 and 44–46 can then sequentially illuminate particles in sample volumes of flow tube 20. Sequential illumination of the particles in the sample volume by multiple illumination morphing elements positioned at various locations can, for example, determine if a particle is shadowing another particle.

Figure 4A:
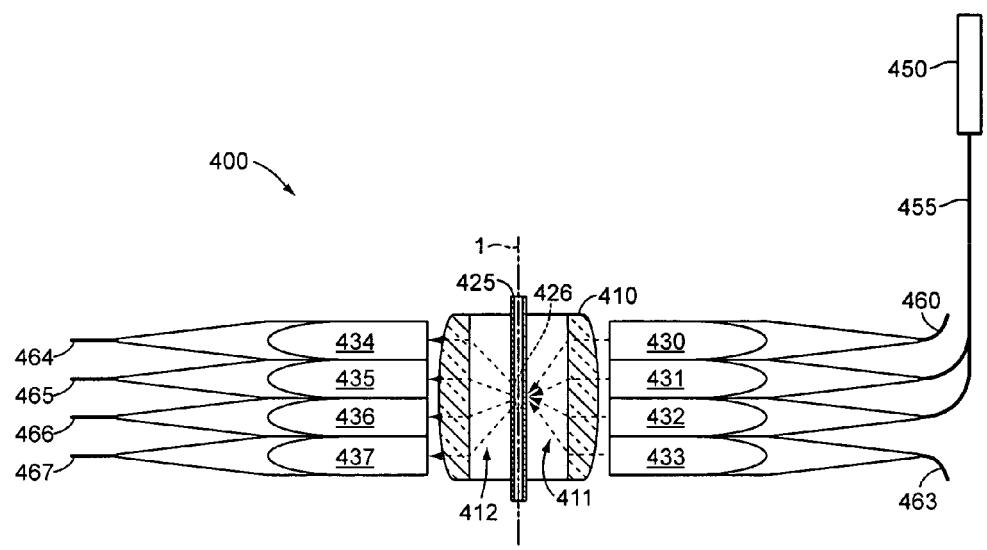
FIG. 4A depicts a sectional view of a particle detection system in accordance with an exemplary embodiment of the invention.

In an exemplary embodiment, a plurality of morphing elements can be disposed circularly around the radial collimator and stacked in one or more tiers. FIG. 4A shows a sectional view, for example 4A—4A of FIG. 1, of a particle detection system 400. Note that the reference numbers for the morphing elements in FIGS. 4A and 4B have been changed from FIG. 1 to clarify depiction of an embodiment with multiple tiers of morphing elements. Particle detection system 400 includes a light source 450, a radial collimator 410, a flow tube 425, a plurality of illumination morphing elements 431–432, and a plurality of detection morphing elements 430 and 433–437. In various embodiments, flow tube 425 and radial collimator 410 can be centered on centerline axis 1.

Figure 4B:
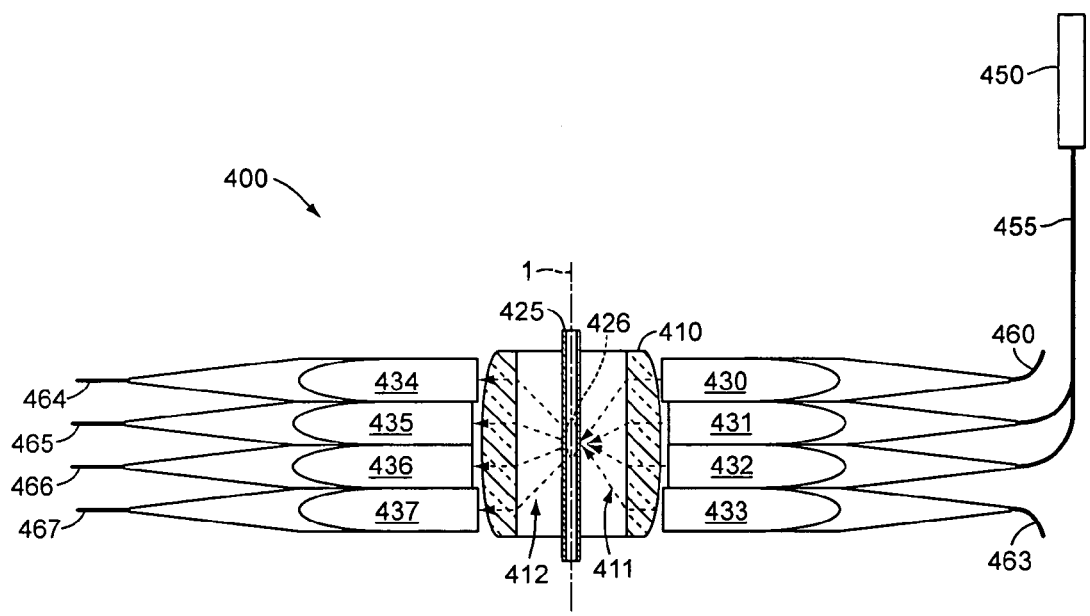
FIG. 4B depicts a sectional view of another particle detection system in accordance with an exemplary embodiment of the invention.
Figure 4C:
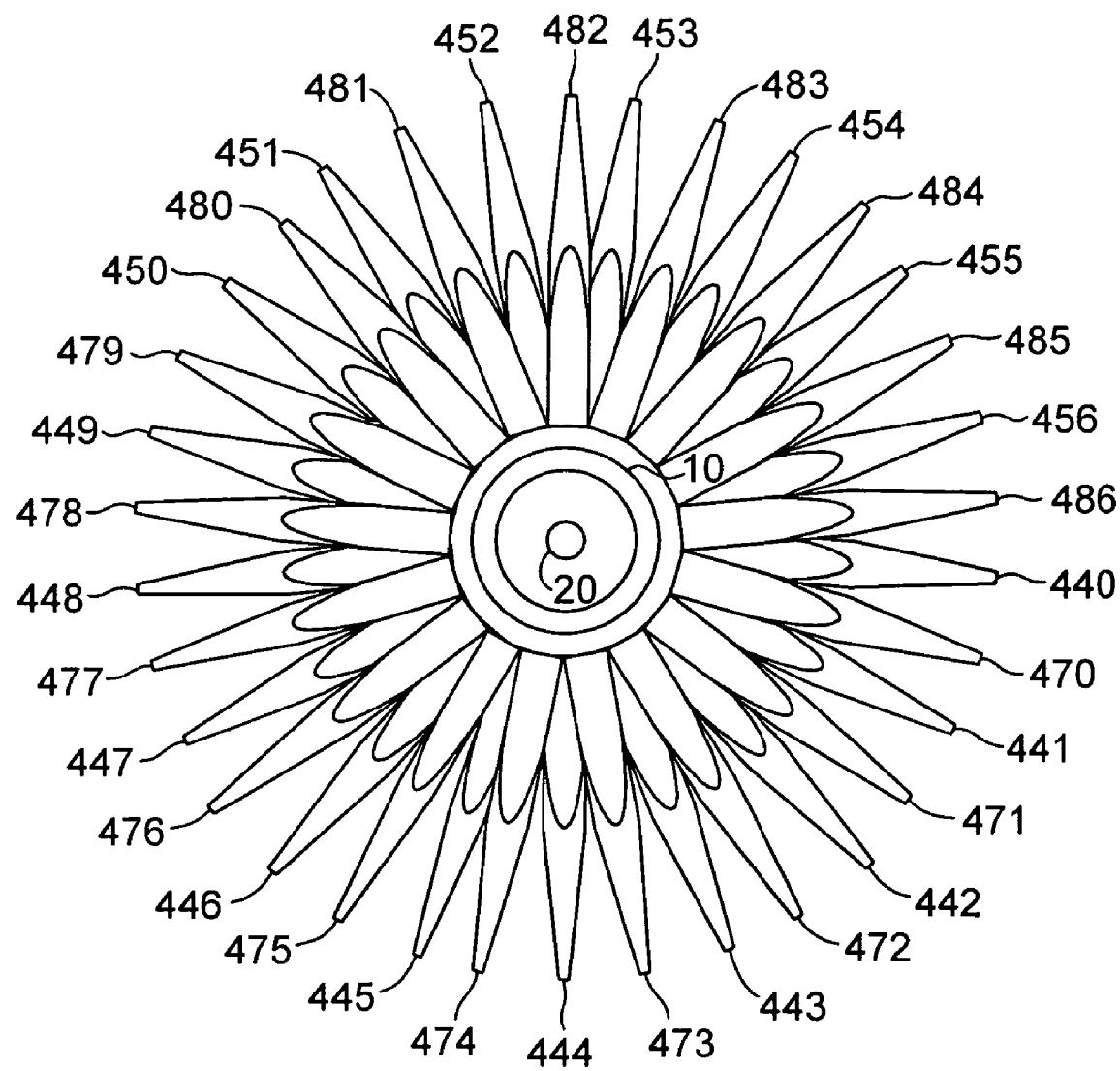
FIG. 4C depicts a top down view of another particle detection system in accordance with an exemplary embodiment of the invention.

Referring again to FIGS. 2 and 3, the cross sectional shape of sections 220 and 320 can be polygonal, such as, for example, hexagonal, triangular, square, or rectangular. This can eliminate or minimize gaps between adjacent morphing elements and between multiple tiers of morphing elements. Eliminating gaps improves light propagation efficiency by preventing light leakage through gaps. Morphing elements can be stacked contiguously and without gaps, as shown in FIG. 4A, if their axes remain parallel and their input port apertures are normal to their axes. In various embodiments, morphing elements in the lower tier can also be off-set from morphing elements in the upper tier. For example, as shown in FIG. 4B, a morphing element in a lower tier does not have to be directly below a morphing element in an upper tier. A lower tier can also be off-set from an upper tier, for example, by rotational symmetry. This is shown by the top down view of FIG. 4C in which lower tier morphing elements 440–456 are off-set from upper tier morphing elements 470–486. Other embodiments comprising multiple tiers can be configured in a similar manner.

In operation, light from light source 450 can be coupled into optical fiber 455. Light from optical fiber 455 can be coupled into light input ends of illumination morphing elements 431 and 432. Light can travel through the illumination morphing elements by total internal reflection and exit from light output ends of illumination morphing elements 431 and 432. The light, represented by lines 411, is focused by radial collimator 410 to a sample volume 426 within flow tube 425. Side scattered light and fluorescence, represented by lines 412, can be collected by radial collimator 410 and coupled into light input ends of detection morphing elements 430 and 433–437. In various embodiments, spectral filtering can be used to discriminate fluorescence from side scattered light. The collected scattered light and fluorescence can then be coupled from the light output ends of detection morphing elements 430 and 433–437 into optical fibers 460 and 463–467. The optical fibers transport the collected scattered light and fluorescence to appropriate detectors (not shown). In various embodiments, the detectors can be gated to receive light after the initial illumination pulse has terminated, for example, when the fluorescence has a decay time, In another exemplary embodiment shown in FIGS. 5A and 5B, a particle detector 500 uses an assembly 541 to capture light, such as, for example, scattered light and fluorescence, and to radially collimate the captured light. As used herein and with reference to FIG. 5A, the term "radially collimate" refers to light rays projected on to radial planes containing axis 1. FIG. 5A depicts a section along 5A—5A of FIG. 5B of a particle detector 500. Particle detector 500 comprises a flow tube 525 that transports particles to a sample volume 520. Flow tube 525 is centered on a centerline axis 1.

In various embodiments, assembly 541 can be arranged around and centered on centerline 1. Referring to FIG. 5A, assembly 541 can comprise a plurality of toroidally shaped lenses arranged in a ring centered on axis 1. These lenses can (a) focus collimated light exiting morphing elements 537 and 538 on sample volume 520 inside flow tube 525 and (b) radially collimate light propagating from sample volume 520 through flow tube 545. In various embodiments, a first lens 543 can be, for example, a toroidal element having a cylindrical outer surface and a convex inner surface. Disposed above first lens 543 can be, for example, second lens 564 and disposed below first lens 543 can be, for example, third lens 544. Second lens 564 and third lens 544 can be toroidal lenses having a convex outer surface and a conical inner surface. As shown in FIG. 5A, the conical inner surfaces of second lens 564 and third lens 544 are disposed such that they work in conjunction with their convex toroidal outer surfaces to project collimated light into morphing elements 535 and 536. One of ordinary skill in the art will understand that one or more of monolithic first lens 543, second lens 564, and third lens 544, can be replaced by a separate elements, such as, for example, a conical lens element in conjunction with a torroidal lens element. Referring to FIG. 5A, illumination morphing elements 537 and 538 couple light from a light source (not shown) to assembly 541. Light from the light source, represented by arrows 511, can be focused by assembly 541 onto sample volume 520.

Light rays 511 can be focused by assembly 541 and light rays 512, representing scattered light and fluorescence from particles within sample volume 520 which are intercepted by assembly 541, are partially collimated when projected on a plane normal to centerline 1. However, when projected on radial planes containing centerline 1 and section 5A—5A of FIG. 5B (which is the view in FIG. 5A), rays 511 focused on the particles by assembly 541 and rays 512 propagating from the particles to detection assembly 541 are not collimated.

Accordingly, FIG. 5A illustrates how optical elements 543, 544, and 564 can focus rays 511 on sample volume 520 and how they can collimate rays 512 propagating from particles in sample volume 520.

Figure 5B:
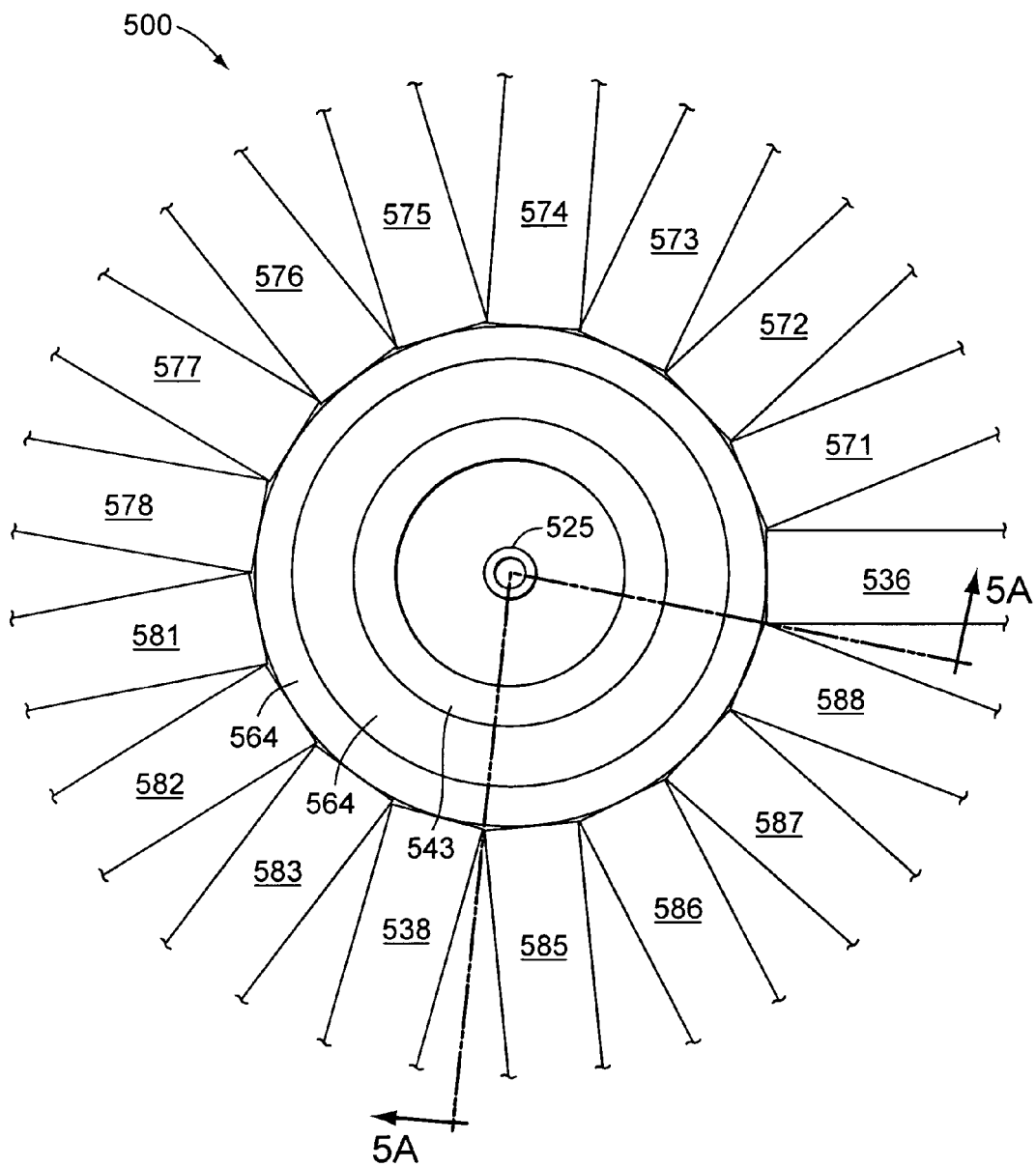
FIG. 5B depicts a top down view of a particle detection system in accordance with an exemplary embodiment of the invention.

In various embodiments, for example, light that projects from elements 537 and 538 and is side scattered by particles in sample volume 520, can propagate and be collected by morphing elements 535 and 536 as shown in FIGS. 5A and 5B. Side scattered light and fluorescence, can also propagate and be detected by morphing elements, such as, for example, elements 577–578 in FIG. 5B. As in other embodiments, spectral filtering can be used to discriminate fluorescence from side scattered light. Forward scattered light and fluorescence can be detected by, for example, morphing elements 573–576.

FIG. 5A depicts a sectional view 5A—5A of FIG. 5B containing centerline 1 at the center of detection assembly 541. Accordingly, light can be radially collimated by a combination of toroidal lenses forming assembly 541. Light radially collimated by assembly 541 passes into detection morphing elements positioned as a first tier 535 and a second tier 536. As shown in FIG. 5A, assembly 541 can further include planar mirrors 519 positioned to bridge gaps between second lens 564 and morphing elements 536 and 538. Because the curvature of lens 564 can cause air gaps to exist between lens 564 and second tier morphing elements 536 and 538, some of the light projected by morphing element 538 can leak out from the air gaps and, thereby, avoid capture by lens 564 and morphing element 536. As shown in FIG. 5A, a planar mirror 519 positioned to bridge the gaps between lens 564 and second tier morphing elements 538 and 536 can reduce this loss of light. In an embodiment, planar mirror 519 can be configured as an annular ring with symmetry about axis 1. Similarly, another planar mirror 519 can be positioned to bridge the gap between third lens 544 and first tier morphing elements 535 and 537. Planar mirrors are not depicted in FIG. 5B for ease of illustration. Although FIGS. 5A and 5B depict particular lenses, one of ordinary skill in the art will understand that other lenses and prisms may be used. For example, the curvature of lenses 543, 544, and 564 can be noncircular in planes containing centerline axis 1. Alternatively, their centers of curvature can be shifted vertically in FIG. 5A.

Figure 6:
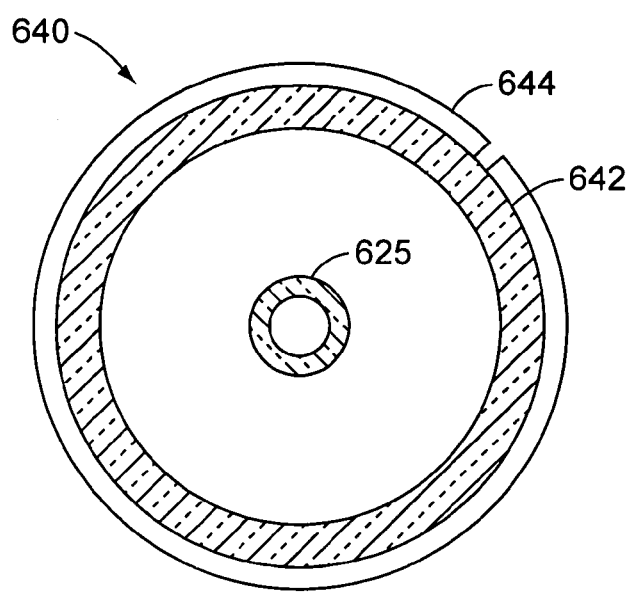
FIG. 6 depicts a top down view of a radial collimator in accordance with an exemplary embodiment of the invention.

FIG. 6 depicts another exemplary embodiment of a radial collimator for a particle detection system. Radial collimator 640 can be centered on flow tube 625. Radial collimator 640 comprises a tube 642 and a fresnel lens 644 around tube 642. Tube 642 can be, for example, a cylindrical glass tube. Fresnel lens 644 can be sufficiently thin and flexible to allow wrapping around tube 642. Thin, flexible Fresnel lenses are made, for example, by Fresnel Technologies, Inc. of Fort Worth, Tex. Fresnel lens 644 can also be softened to permit wrapping by heating. In an embodiment, Fresnel lens 644 is a cylindrical type of Fresnel lens. When wrapped around cylindrical glass tube 642, grooves of Fresnel lens 644 can be oriented circumferentially around tube 644 and in planes normal to the tube axis.

Figure 8:
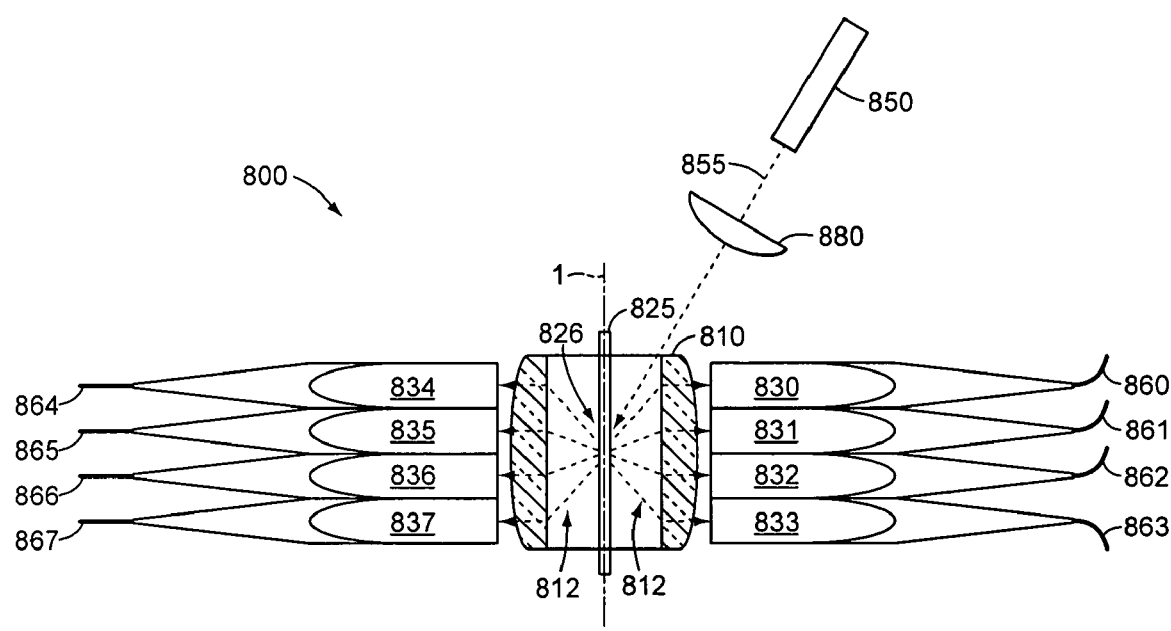
FIG. 8 depicts a sectional view of a particle detection system in accordance with an exemplary embodiment of the invention.

FIG. 8 depicts another exemplary embodiment of a radial collimator for a particle detection system. A particle detection system 800 includes a light source 850, a radial collimator 810, a flow tube 825, an optical element 880, and a plurality of detection morphing elements 830–837. In various embodiments, flow tube 825 and radial collimator 810 can be centered on centerline axis 1.

In operation, a light 855 from light source 850 can be directed to sample volume 826 by optical element 880. Rather than using radial collimator 810 to focus light onto sample volume 826, optical element 880 can be used. One of ordinary skill in the art will understand that optical element 880 can be replaced by other optical elements and combinations of optical elements, such as, for example, multiple lenses, prisms, optical fibers, and/or mirrors to focus the light onto sample volume 826. Scattered light and fluorescence, represented by lines 812, can be collected by radial collimator 810 and coupled into light input ends of detection morphing elements 830–837. The collected scattered light and fluorescence can then be coupled from the light output ends of detection morphing elements 830–837 into optical fibers 860–867. The optical fibers transport the collected scattered light and fluorescence to appropriate detectors (not shown).

It will be apparent to those skilled in the art that the illumination systems and methods described in the present invention can be used to illuminate multiple locations remote from a single light source. It will be also apparent to those skilled in the art that various modifications and variations can be made in the disclosed process without departing from the scope or spirit of the invention. For example, one of skill in the art of optical design can approximate the function of the morphing element from imaging optics and yet still embody the spirit of the present invention that describes a solution comprising non-imaging optics. Other embodiments of the invention will be apparent to those skilled in the art from consideration of the specification and practice of the invention disclosed herein. It is intended that the specification and examples be considered exemplary only, with a true scope of the invention being indicated by the following claims.

What is claimed is:

1. A particle detector comprising:
   at least one detector;
   a light source that provides light;
   a radial collimator disposed surrounding a sample volume;
   an illumination morphing element comprising a light output end adjacent to the radial collimator and a light input end coupled to the light source; and
   a plurality of detection morphing elements, each of the plurality of detection morphing elements comprising a light input end adjacent to the radial collimator and a light output end coupled to one or more of the at least one detectors.

2. The particle detector of claim 1, wherein each of the plurality of detection morphing elements further comprises a first portion having a polygonal shape and a second portion having a conical shape.

3. The particle detector of claim 1, wherein each of the plurality of detection morphing elements further comprises a cylindrical Fresnel lens adjacent to the light input end.

4. The particle detector of claim 1, wherein the light input end of each of the plurality of detection morphing elements has a convex shape.

5. The particle detector of claim 1, wherein the plurality of morphing elements surrounding the sample volume are arranged in a plurality of tiers.

6. The particle detector of claim 1, wherein the radial collimator comprises a barrel-shaped lens having a cylindrical inner surface and a convex outer surface.

7. The particle detector of claim 1, wherein the radial collimator comprises a tube and a Fresnel lens.

8. The particle detector of claim 1, wherein the radial collimator comprises a plurality of assemblies, wherein each of the plurality of assemblies comprises a plurality of lenses.

9. The particle detector of claim 8, further comprising at least one planar mirror to reduce light loss in at least one of the plurality of assemblies.

10. The particle detector of claim 1, further comprising a flow tube that carries a plurality of particles through the sample volume.

11. The particle detector of claim 1, wherein the light source is selected from a laser, an ultra violet lamp, and an LED.

12. The particle detector of claim 1, wherein the light input end of the illumination morphing element is coupled to the light source by an optical fiber.

13. The particle detector of claim 1, wherein each of the light output ends of the plurality of detection morphing elements is coupled to a detector element by optical fibers.

14. A particle detector comprising:
    a detector;
    a light source that provides light;
    a radial collimator disposed surrounding a sample volume;
    a plurality of illumination morphing elements, each of the plurality of illumination morphing elements comprising a light output end adjacent to the radial collimator and a light input end coupled to the light source; and
    a plurality of detection morphing elements, each of the plurality of detection morphing elements comprising a light input end adjacent to the radial collimator and a light output end coupled to the detector.

15. The particle detector of claim 14, wherein each of the plurality of illumination morphing elements is disposed at a predetermined position proximate the radial collimator.

16. The particle detector of claim 14, wherein each of the plurality of detection morphing elements further comprises a first portion having a polygonal shape and a second portion having a conical shape and wherein the plurality of detection morphing elements are disposed proximate the radial collimator in a plurality of tiers.

17. The particle detector of claim 14, further comprising a flow tube that carries samples to the sample volume.

18. The particle detector of claim 17, wherein a portion of the flow tube is disposed along an axis of the radial collimator.

19. A particle detecting method comprising:
    providing a barrel-shaped lens surrounding a sample volume;
    coupling a light from a light source to at least one illumination morphing element, wherein the illumination morphing element directs the light onto the barrel-shaped lens;
    directing the light onto the sample volume using the barrel-shaped lens;
    collecting a sample light emitted by a plurality of particles that passes through the sample volume using the barrel shaped lens;
    coupling the collected sample light to a plurality of detection morphing elements disposed adjacent to the barrel-shaped lens;
    directing the sample light from the plurality of detection morphing elements to a first detector.

20. The method of claim 19, wherein the sample light comprises at least one of scattered light and fluorescence.

21. The method of claim 20, wherein collected scattered light is directed to the first detector.

22. The method of claim 20, wherein collected fluorescence is directed to at least a second detector.

23. The method of claim 19, wherein the plurality of particles are transported through the sample volume by a liquid in a flow tube.

24. The method of claim 23, further comprising using the plurality of illumination morphing elements to sequentially illuminate the sample volume.

25. The method of claim 19, further comprising coupling light from the light source to a plurality of illumination morphing elements.

26. A particle detector comprising:
at least one detector;
a light source that provides light;
at least one optical element disposed to direct light from the light source to a sample area;
a radial collimator disposed surrounding the sample volume; and
a plurality of detection morphing elements, each of the plurality of detection morphing elements comprising a light input end adjacent to the radial collimator and a light output end coupled to one or more of the at least one detectors.

27. The particle detector of claim 26, wherein each of the plurality of detection morphing elements further comprises a first portion having a polygonal shape and a second portion having a conical shape.

28. The particle detector of claim 26, wherein the plurality of morphing elements surrounding the sample volume are arranged in a plurality of tiers.

29. The particle detector of claim 26, wherein the radial collimator comprises a barrel-shaped lens having a cylindrical inner surface and a convex outer surface.

30. The particle detector of claim 26, wherein the radial collimator comprises a tube and a Fresnel lens.

31. The particle detector of claim 26, wherein the radial collimator comprises a plurality of assemblies, wherein each of the plurality of assemblies comprises as least one lens.

32. The particle detector of claim 26, wherein the light source is selected from a laser, an ultra violet lamp, and an LED.

33. The particle detector of claim 26, wherein the at least one optical element comprises a lens.

* * * * *